DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED JULY 1, 1975

936 O.G. 7

T936,001

NOVEL HYDROXYL-TERMINATED POLYMERS

Robin Nikolas Greene, Apt. 4, 1425 State Run Road,
New Albany, Ind. 47120

Filed Mar. 12, 1974, Ser. No. 450,357
Int. Cl. C07c *31/18*
U.S. Cl. 260—635 R
No Drawing. 16 Pages Specification Liquid, random ethylene/$C_3$–$C_{20}$ $\alpha$-olefin copolymers having an average hydroxyl functionality of about 1.8–3.0 and a number-average molecular weight of about 300–3500, useful as starting materials for the preparation of high molecular weight polyurethanes and polyesters, are made from random ethylene/$C_3$–$C_{20}$ $\alpha$-olefin copolymers (having about 1.8–3.0 carboxylic groups, 1.0–1.5 chain ester groups, 0.4–1 chain ketone groups, and 1.0–2.0 chain hydroxyl groups per molecule on the average) by a process involving the following consecutive steps:

(1) treating the carboxyl-containing copolymer at about 20° C. to about 100° C. in an inert solvent with about 5–10 moles each of $PCl_3$ and $PCl_5$ per mole of polymer to convert substantially all hydroxyl groups to chloride and carbonyl groups to *gem*-dichloride;

(2) removing excess phosphorus chlorides;

(3) contacting the polymeric product of (1) in an inert dry solvent (preferably tetrahydrofuran) with about 3–6 moles of $LiAlH_4$ and 10–60 moles of LiH per mole of polymer to reduce substantially all carboxyl, carboxylic acid chloride, and ester groups to hydroxyl groups and all *gem*-dichloride groups to methylene groups; and (4) decomposing the unchanged metal hydrides with water or alcohol (preferably in the presence of ions of a neutral metal salt such as NaCl) and recovering the hydroxyl-substituted polymer.